United States Patent
Dreher et al.

(10) Patent No.: US 8,388,137 B2
(45) Date of Patent: Mar. 5, 2013

(54) SYSTEM AND METHOD FOR ANALYZING WAVEFRONT ABERRATIONS

(75) Inventors: Andreas W. Dreher, Escondido, CA (US); Shui T. Lai, Encinitas, CA (US)

(73) Assignee: Ophthonix, Inc., Vista, CA (US)

(*) Notice: Subject to any disclaimer, the term of this patent is extended or adjusted under 35 U.S.C. 154(b) by 0 days.

(21) Appl. No.: 13/099,190

(22) Filed: May 2, 2011

(65) Prior Publication Data

US 2011/0255053 A1    Oct. 20, 2011

Related U.S. Application Data

(62) Division of application No. 12/755,352, filed on Apr. 6, 2010, now Pat. No. 7,954,950, which is a division of application No. 11/064,382, filed on Feb. 22, 2005, now abandoned.

(60) Provisional application No. 60/546,378, filed on Feb. 20, 2004.

(51) Int. Cl.
*A61B 3/00* (2006.01)
(52) U.S. Cl. .......... 351/246; 351/211; 351/212
(58) Field of Classification Search ............ 351/246, 351/247, 200, 211, 212
See application file for complete search history.

(56) References Cited

U.S. PATENT DOCUMENTS

| | | |
|---|---|---|
| 6,761,454 B2 | 7/2004 | Lai et al. |
| 6,781,681 B2 | 8/2004 | Horwitz |
| 6,786,602 B2 | 9/2004 | Abitbol |
| 7,771,048 B2 | 8/2010 | Dai et al. |
| 2003/0133074 A1 | 7/2003 | Pettit et al. |
| 2003/0133075 A1 | 7/2003 | Sheets et al. |
| 2004/0054358 A1 | 3/2004 | Cox et al. |
| 2004/0263786 A1 | 12/2004 | Williams et al. |

FOREIGN PATENT DOCUMENTS

| | | |
|---|---|---|
| EP | 1 327 948 | 7/2003 |
| EP | 1 327 949 | 7/2003 |
| JP | 2003-245299 | 9/2003 |
| JP | 2003-245301 | 9/2003 |
| WO | WO-01/89424 | 11/2001 |
| WO | WO-02/088830 | 11/2002 |
| WO | WO-03/050594 | 6/2003 |
| WO | WO-03/082162 | 10/2003 |
| WO | WO-2004/072709 | 8/2004 |

OTHER PUBLICATIONS

Supplementary European Search Report for EP 05723711.7, mailed Jul. 10, 2009, 3 pages.
Dreiseitl and Ohno-Machado, Journal of Biomedical Informatics (2002) 35:352-359.

*Primary Examiner* — Hung Dang
(74) *Attorney, Agent, or Firm* — Morrison & Foerster LLP

(57) ABSTRACT

A method of creating a statistical model for use in predicting vision correction prescriptions for patients is disclosed. The method comprises obtaining a plurality of wavefront aberration measurements from a plurality of patient's eyes, obtaining a plurality of visual acuity measurements from the plurality of patients, applying values associated with the plurality of wavefront measurements to an input layer of a statistical model, applying values associated with the plurality of visual acuity measurements to an output layer of the statistical model, and generating a plurality of weight values associated with respective nodes of the statistical model based on the applied values associated with the plurality of wavefront measurements and corresponding values associated with the plurality of visual acuity measurements.

19 Claims, 8 Drawing Sheets

US 8,388,137 B2

SYSTEM AND METHOD FOR ANALYZING WAVEFRONT ABERRATIONS

RELATED APPLICATIONS

The present application is a divisional application of Application No. 12/755,352, filed on Apr. 6, 2010, now U.S. Pat. No. 7,954,950 which is a divisional application of Application No. 11/064,382, filed on Feb. 22, 2005, now abandoned, which claimed the benefit of priority under 35 U.S.C. §119(e) to U.S. Provisional Patent Application Ser. No. 60/546,378, entitled "SYSTEM AND METHOD FOR ANALYZING WAVEFRONT ABERRATIONS," filed on Feb. 20, 2004. Each of the foregoing patents and applications is hereby incorporated by reference in its entirety.

This application is related to U.S. patent application Ser. No. 10/218,049, entitled "Apparatus and Method of Correcting High order Aberrations of the Human Eye," filed Aug. 12, 2002; U.S. patent application Ser. No. 10/076,218, entitled "Apparatus and Method for Determining Objective Refraction using Wavefront Sensing," filed Feb. 13, 2002, issued as U.S. Pat. No. 6,761,454; and U.S. patent application Ser. No. 10/014,037, entitled "System and Method for Wavefront Measurement," filed Dec. 10, 2001, issued as U.S. Pat. No. 6,781,681. Each of the foregoing patents and applications is hereby incorporated by reference in its entirety.

BACKGROUND OF THE INVENTION

1. Field of the Invention

The present invention relates to a system and method for correcting aberrations of the human eye. More particularly, the invention relates to method and system for statistically correlating objective measurements of aberrations associated with the human eye with subjective measurements of visual acuity to create a statistical model that can be used to predict vision correction prescriptions based at least in part on objectively measured aberrations of a patient's eye.

2. Description of the Related Art

The human eye, namely the cornea and lens, can exhibit a variety of optical aberrations that diminish the optical performance of the eye, resulting in blurred vision. The correction of blurred vision by lenses has typically been limited to correction of low order aberrations only, such as defocus and astigmatism. Traditionally, high order aberrations, e.g. those describable with Zernike polynomials of the third order or higher, could not be corrected using lenses. In addition, due to lens manufacturing limitations and expenses, defocus and astigmatism are typically only corrected in discrete steps, with any correction being made to the nearest one quarter (¼) diopter. Unfortunately, the resolution of one quarter (¼) diopter results in incomplete vision corrections and limits the performance of the patient's eye.

Recently, systems employing wavefront aberrometry, such as described in the co-pending patent applications incorporated herein, have enabled the high order aberrations in a patient's eyes to be measured objectively, accurately, and rapidly. When coupled with a custom aberrator that is adapted to correct some or all of the high order aberrations in a patient's eyes, such as also described in the co-pending patent applications incorporated herein, a patient's visual acuity may be improved to as well as 20/10.

BRIEF SUMMARY OF THE INVENTION

The invention relates to correlating or establishing a relationship between objectively measured values or parameters of a patient's eyes with subjectively measured or reported values or parameters of visual performance.

In one embodiment, this correlation is performed via machine learning techniques that create a statistical model (e.g., a neural network).

In another embodiment, a method for specifying a vision correction prescription for a patient's eye, comprises: obtaining a wavefront aberration measurement of a patient's eye; applying at least one value from the wavefront aberration measurement to a statistical model trained to analyze the at least one value; and predicting a vision correction prescription for the patient's eye based at least in part on the analysis of the at least one value by the statistical model.

In a further embodiment, a method of predicting a difference in visual acuity resulting from high order correction versus standard correction of a patient's eyes, comprises: obtaining a wavefront aberration measurement of a patient's eye; inputting at least one value derived from the wavefront aberration measurement into a statistical model trained to analyze the at least one value; and predicting a difference in visual acuity resulting from high order correction versus standard correction of a patient's eyes, based on the at least one value and the statistical model.

In yet another embodiment, the invention provides a method of creating a statistical model for use in predicting vision correction prescriptions for patients, the method comprising: obtaining a plurality of wavefront aberration measurements from a plurality of patient's eyes; obtaining a plurality of visual acuity measurements from the plurality of patients; applying values associated with the plurality of wavefront measurements to an input layer of a statistical model; applying values associated with the plurality of visual acuity measurements to an output layer of the statistical model; and generating a plurality of weight values associated with respective input nodes of the input layer based on the applied values associated with the plurality of wavefront measurements and corresponding values associated with the plurality of visual acuity measurements.

In a further embodiment, the invention provides a learned data structure created using the above method of creating a statistical model.

In a further embodiment, the invention provides a computer readable medium that stores computer executable code, which when executed performs a method for specifying a vision correction prescription for a patient's eye, the method comprising: obtaining a wavefront aberration measurement of a patient's eye; applying at least one value derived from the wavefront aberration measurement to a statistical model trained to analyze the at least one value; and predicting a vision correction prescription for the patient's eye based on the at least one value and the statistical model.

In another embodiment, a system for specifying a vision correction prescription for a patient's eye, comprises: means for obtaining a wavefront aberration measurement of a patient's eye; and means for analyzing at least one value derived from the wavefront aberration measurement to predict a vision correction prescription for the patient's eye based at least in part on the at least one value.

DETAILED DESCRIPTION OF THE INVENTION

Figure 1:
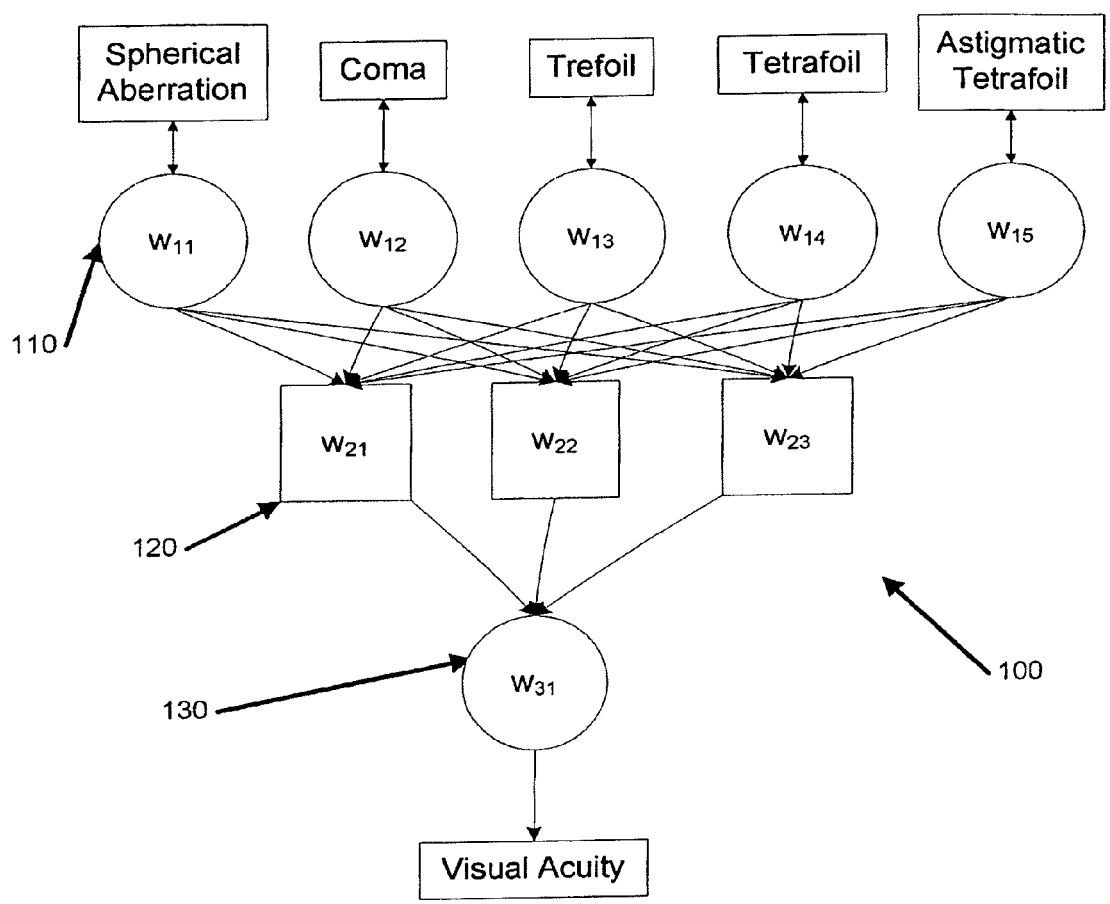
FIG. 1 graphically depicts one embodiment of a neural network for predicting visual acuity based on measured aberrations in a patient's eye.

The following detailed description is directed to certain specific embodiments of the invention. However, the invention can be embodied in a multitude of different ways as defined and covered by the claims. In this description, reference is made to the drawings wherein like parts are designated with like numerals throughout.

One practical disadvantage of the objective wavefront aberration measurements, expressed in terms of Zernike polynomials, is that these polynomials may be difficult to correlate with a subjective refraction measurement made by a eye care professional, such as from using a phoropter, a Snellen chart, and a patient's feedback. This tends to make it difficult for the eye care professional to make an informed recommendation to the patient of a course of action for correcting the patient's vision.

Theoretically, wavefront aberrometry measurements of low-order aberrations in a patient's eyes should correspond to the traditional prescription of sphere, cylinder, and axis. However, interaction of high order aberrations may contribute to the patient's perceived blur on the retina, and therefore should be accounted for in predicting "subjective" measures of visual performance. Subjective measures of visual performance include, for example, Snellen visual acuity, based on a patient's ability to read letters of decreasing size in rows of a Snellen chart, and contrast sensitivity.

Ideally, if all aberrations of a patient's eye are corrected, a diffraction-limited image is formed on the retina of the patient's eye. The visual acuity of the eye is then determined by the entrance size of the pupil. Thus, methods of predicting subjective measures of visual performance from objective high order aberration data have focused on algorithms based on maximizing the optical quality (or minimizing the blur) of light being focused on a patient's eye.

However, performance of a human's visual system is dependent on both the optical properties of the eye and on the neurological response by the patient's retina and brain. Moreover, it has been found that the presence of some degree of certain high order aberrations, which technically increase the blur at a patient's retina, actually improve subjective measures of a patient's visual performance. For example, studies of the eyes of people with 20/15 or better natural visual acuity have found the presence of high order aberrations to be relatively common despite these people's high visual acuity. This result contradicts the theory behind using optical quality based algorithms to predict visual acuity. Rather, subjective visual acuity is therefore determined by many factors such as the observable wavefront aberrations of a patient's eyes, interactions between each aberration in a patient's eyes, and interactions between the aberrations and the patient's neurological visual processing path.

Machine learning techniques have been applied in a variety of fields, including financial forecasting, business decision making, medical diagnosis, and pattern recognition, to make predictions where direct observation of all relevant factors is not possible. In particular, inductive learning techniques take as input a training set of observed data points to "learn" an equation, a set of rules, or some other data structure. This learned structure or statistical model may then be used to make generalizations about the training set or predictions about new data. As used herein, "statistical model" refers to any learned and/or statistical data structure that establishes or predicts a relationship between two or more data parameters (e.g., inputs and outputs). Although the invention is described below with reference to neural networks, other types of statistical models may be employed in accordance with the present invention.

For example, each data point of the training data set may include a set of values that correlate with, or predict, another value in the data point. Thus, in a medical diagnosis application, a set of biometrics, such as blood pressure and age, of heart attack patients may predict a five-year likelihood of another heart attack. By using, as a training set, data points consisting of measurements of the biometric values along with the actual outcome for each patient, an inductive learning technique may construct a data structure that, when given a new patient's biometrics, predicts the new patient's five-year likelihood of another heart attack.

Inductive learning methods that are well known to those of skill in the art include techniques such as, for example, Bayesian reasoning, memory based density estimation, parametric density estimation, and neural networks. In neural networks, a training set is used to learn weights attached to a data structure comprising a network. See, e.g., *Neural Networks for Pattern Recognition*, Christopher M. Bishop (Oxford University Press, 1995). A neural network generally includes a set of nodes for inputting data values, the input layer, and an output layer for producing a predicted data value. Back-propagation neural networks also comprise one or more hidden layers, between the input and output layers. The input layer and each hidden layer are represented as having outputs to each node of the next layer, either another hidden layer or an output layer. After training is complete, the neural network comprises a set of weights for each node in the network. These weight values express a relationship between the training data that is applied to input nodes and training data applied to output nodes, as well as any hidden layer node values. Using this trained relationship, the neural network can predict one or more output values when new input values or parameters are fed into corresponding nodes of the input layer. For each node, a weight for the node is applied as a coefficient to a fixed equation that expresses the trained relationship (which may vary in different embodiments of the neural network) relating each of the node's inputs to at least one output value. The output value of one or more output layer nodes constitutes the output of the network.

It is to be appreciated that while certain embodiments are discussed with respect to a particular neural network topology, other network topologies, such as, for example, having different numbers of hidden layers, or differing numbers of input or output nodes, can also be used. Further, while certain embodiments are discussed with respect to using neural networks, other inductive machine learning techniques or statistical analysis techniques, such as, for example, those mentioned above, can be used.

FIG. 1 depicts one embodiment of a neural network 100 adapted for receiving wavefront aberration data having five input nodes 110, a hidden layer with three nodes 120, and one output layer with a single node 130 for producing a predicted visual acuity value. Embodiments of the neural network 100 adapted to receive a different number, or all, of the measured wavefront aberrations generally include one input node per wavefront aberration. Embodiments of the neural network 100 may be implemented to execute on any general purpose or specialized computer processor. It is also to be appreciated that the neural network 100 may be implemented in software, which may itself be produced using any computer language or environment, including general-purpose languages such as C or FORTRAN. Preferably, the neural network software is generated using a neural network development tool such as, for example, Brainmaker Pro, produced by California Scientific Software, Nevada City, Calif.

Figures 2, 3:
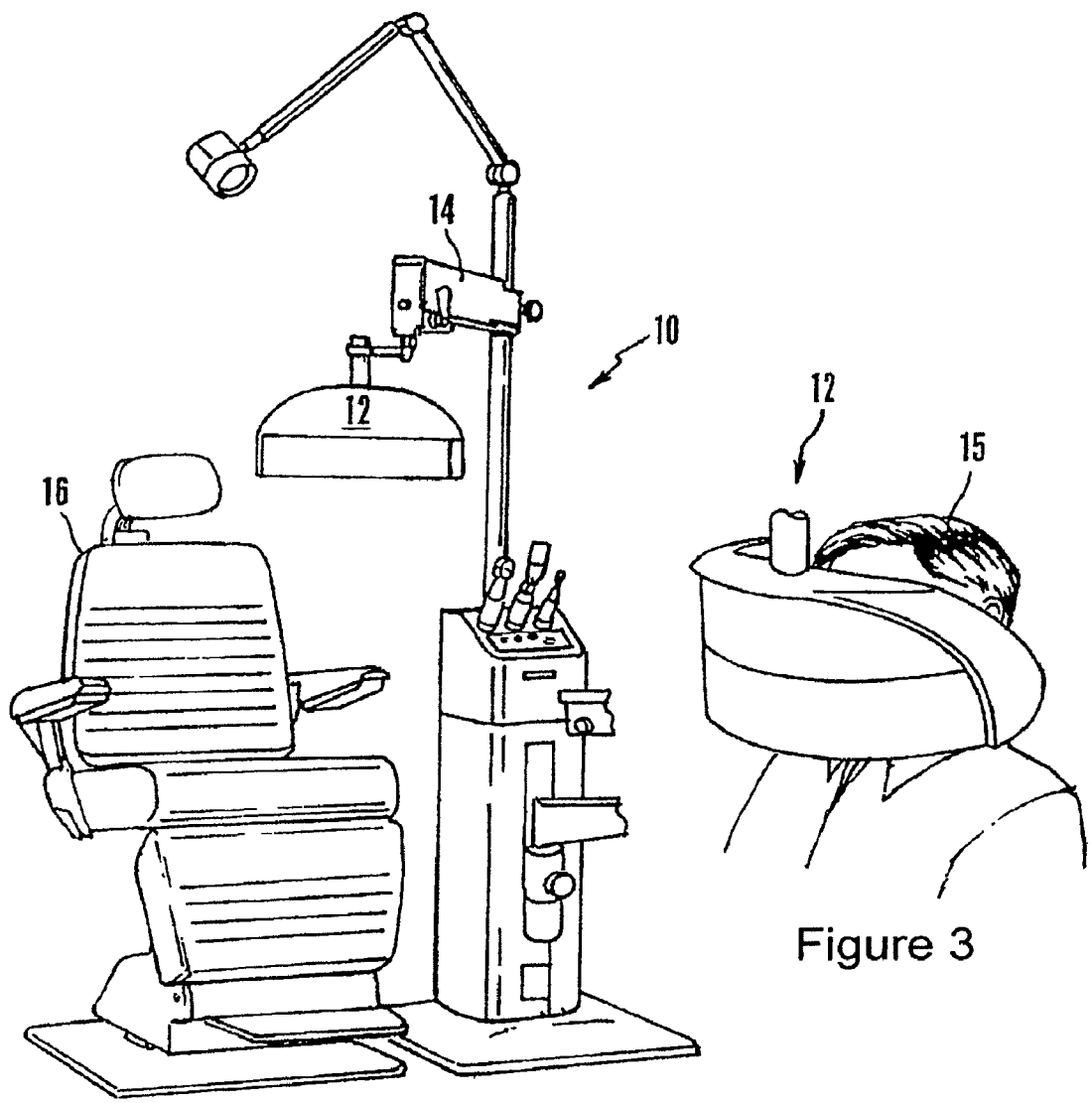
FIG. 2 is a perspective view of one embodiment of an apparatus for measuring wavefront aberrations in a human eye.
FIG. 3 is a detailed perspective view of a portion of the apparatus of FIG. 2 being operated in conjunction with a patient.
Figure 4:
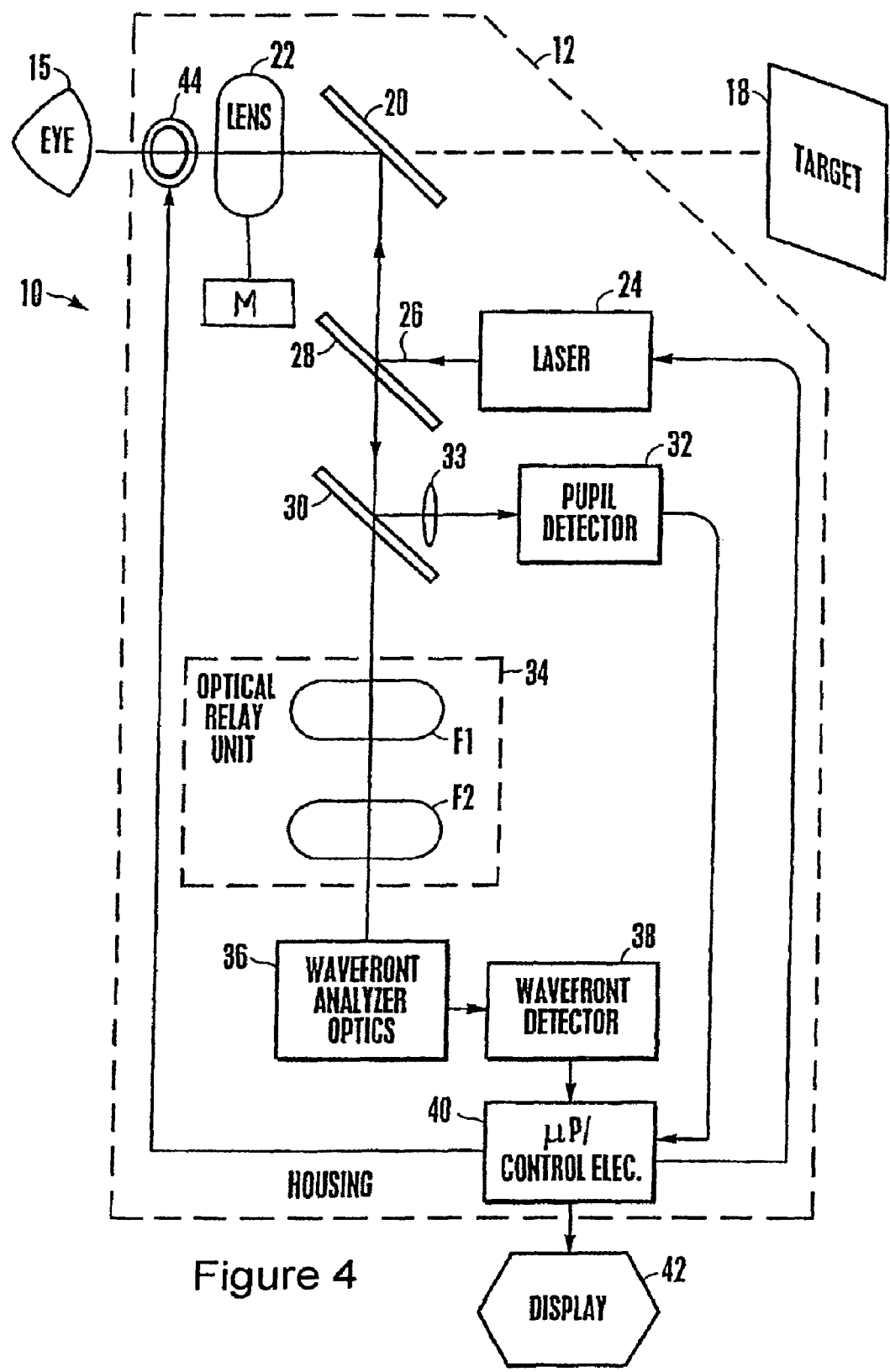
FIG. 4 is a block diagram depicting the components of the apparatus of FIG. 2.

FIGS. 2 and 3 depict one embodiment of an apparatus for measuring wavefront aberrations in a patient's eyes both to collect the training data for the neural network 100 and for subsequent use in conjunction with the neural network 100. The apparatus 10, as described in more detail in the co-pending patent applications incorporated herein, comprises a housing 12 that may be mounted on a movable stand 14, for positioning the housing 12 in front of a patient 15 who may sit in an examination chair 16. In one embodiment, the apparatus 10 may also comprise a phoropter (not pictured). In one embodiment depicted in FIG. 4, the housing 12 comprises a set of optics that is configured to measure wavefront aberrations in the eye of patient 15. It is appreciated by those of skill in the art that there exist different devices, systems and techniques, such as a Schemer disk wavefront sensor, Shack-Hartmann wavefront sensor, Fizeau interferometer, Twymann-Green interferometer, holographic element wavefront sensor, binocular wavefront sensor, etc., for measuring aberrations of the human eye, or other optical systems. Any of these wavefront measuring devices, systems and/or techniques may be utilized in accordance with the present invention.

Using the collected training data, one embodiment of the neural network 100 has been trained using a set of data relating the measured wavefront aberrations of a patient to one measure of visual acuity, e.g., the best corrected spectacle visual acuity (BCSVA), of the patient. A learning set comprising patient aberrations corresponding to the Zernike polynomials that are generally known in the art as spherical aberration, coma, trefoil, tetrafoil, and astigmatic tetrafoil as input values and BCSVA values as the output values was constructed for 85 myopic eyes and 167 astigmatic eyes. The resulting trained neural network predicted visual acuity in a random subset of the data set accurately in 85% of the test cases. In other embodiments, improved accuracy may be obtained in some circumstances by including a greater number of, or all, measured high order aberrations during training and subsequent testing. Furthermore, in other embodiments additional output values, such as contrast sensitivity are used to train an embodiment of the network 100 to obtain greater accuracy. It is appreciated that other measures of visual acuity such as best corrected visual acuity of a patient's eye using contacts, intraocular lenses or Laser In Situ Keratomileuis (LASIK), for example, may also be used as training data for the neural network 100.

Figure 5:
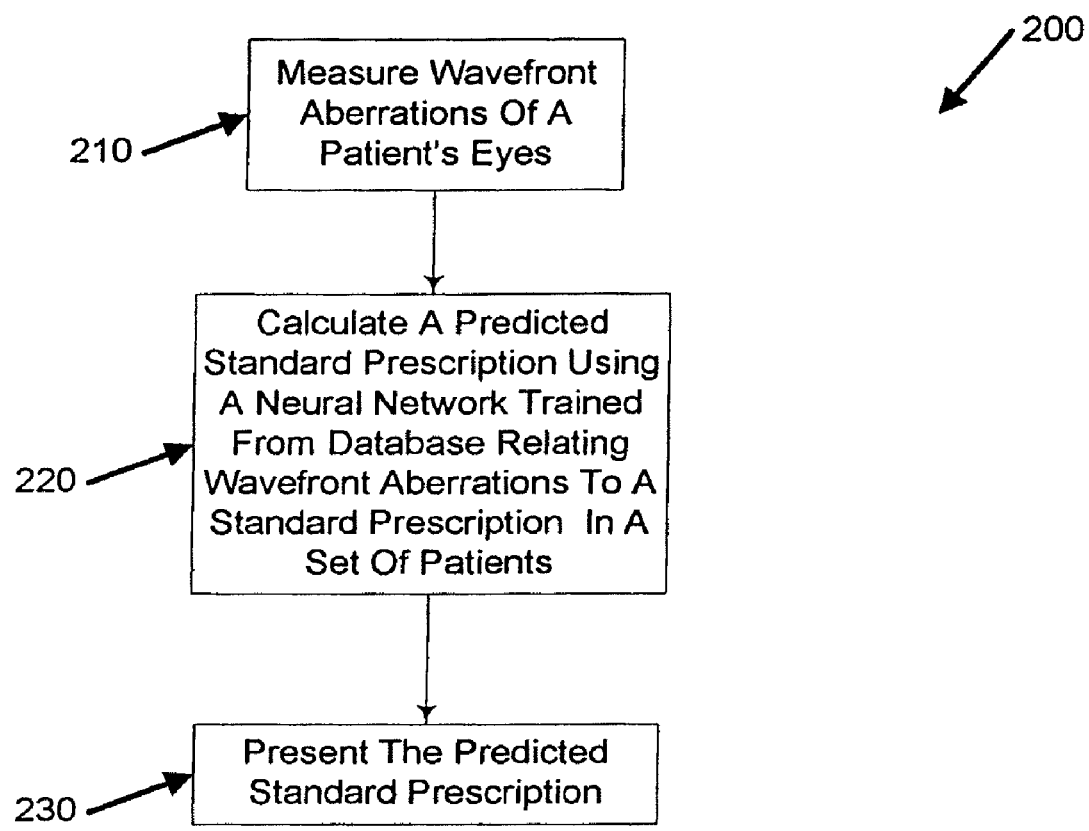
FIG. 5 is a flow chart depicting one embodiment of a process for predicting a standard prescription in a patient by using an embodiment of a neural network similar to that of FIG. 1.

FIG. 5 is a flow chart depicting one embodiment of a process 200 for predicting a standard prescription in a patient based on objectively measured aberrations rather than a subjective phoropter test. A standard prescription, the patient's subjective refraction measure, comprises measurements of sphere, cylinder, and axis, which correspond to low order aberrations. However, as discussed above, subjective measures of visual acuity may also be affected in a particular eye by the interaction of higher order aberrations and the patient's neurological visual path. A training set of patients is first measured to objectively determine the aberrations in their eyes. The subjective refraction of each training patient is also measured by using, for example, a phoropter and a Snellen Chart. In one embodiment, the neural network 100 is trained using the objectively measured aberrations as input and the subjective measurements of sphere, cylinder, and axis as output. It is appreciated that any number of additional data parameters that may have some bearing on a patient's visual acuity can be used to train and create a statistical model in accordance with the present invention. For example, in one embodiment, factors or parameters such as a patient's age, a patient's preferences for improving vision (e.g., improved long distance vision, improved short distance vision, improved contrast, improved resolution of fine detail, improved depth of focus, etc.), and information concerning the patient's prescription history, for example, may serve as training data for building a statistical model. Additionally, parameters or factors such as whether a patient experiences headaches, blurred vision or "halos" at night, or other side effects or symptoms (favorable or unfavorable), can be taken into account during training of the statistical model. These types of data parameters are generally referred to herein as "patient personal profile parameters" or "profile parameters."

After a statistical model has been trained, the model may then be used to predict a prescription of a new patient. Such a process 200 begins at a step 210 where the aberrations of the patient's eyes are objectively measured using, for example, the measurement apparatus 10. Moving on to a step 220, the patient's aberration measurements are input into the trained network 100 which is run to produce predicted sphere, cylinder, and axis measurements based at least in part on objectively measured aberration parameters. These predicted values of sphere, cylinder and axis may then be used, for example, to provide a patient with a standard prescription based at least in part on objective measurements or parameters, to allow the patient and doctor to compare different treatment options (e.g., corrective lenses, contacts or surgery), or in the formulation of a LASIK scheme, for example, to confirm a subjectively measured prescription before executing the LASIK procedure.

It is further appreciated that the statistical model can express relationships between various high order aberrations and visual acuity such that the relative impact of certain high order aberrations and/or combinations thereof can be predicted. For example, certain high order aberrations or combinations of aberrations may consistently reveal poor vision or superior vision among patients having such aberrations. This would indicate that such aberrations or combinations thereof may contribute to the poor or superior vision. Given such a statistical model, it is easy to see how a predicted visual correction prescription may be generated that not only corrects for standard low order aberrations (sphere, cylinder and axis) but also indicates which high order aberrations (e.g., spherical aberration, coma, trefoil, tetrafoil, astigmatic tetrafoil) and/or combinations thereof may be beneficial, detrimental or neutral to a patient's subjectively perceived visual acuity.

It has been further found that different high order aberrations have different levels of importance for myopic, hyperopic, presbyopic, and astigmatic eyes. Thus, in one embodiment of process 200, a different neural network 100 may be used for eyes in each of those categories of eyes. For example, in one embodiment, a neural network 100 may be trained using primarily patients with astigmatic eyes, resulting in a statistical model that is customized especially for patients having astigmatic aberrations.

As discussed above, it has been found that not all high order aberrations have a negative impact on visual acuity. Thus, eye correction techniques or devices that correct high order aberrations such as eyeglasses or contact lenses, for example, containing custom wavefront aberrators, as described in the co-pending patent applications incorporated herein, may be further improved by correcting only those aberrations that have a negative affect on visual acuity, and leaving those that have a positive affect.

Figure 6:
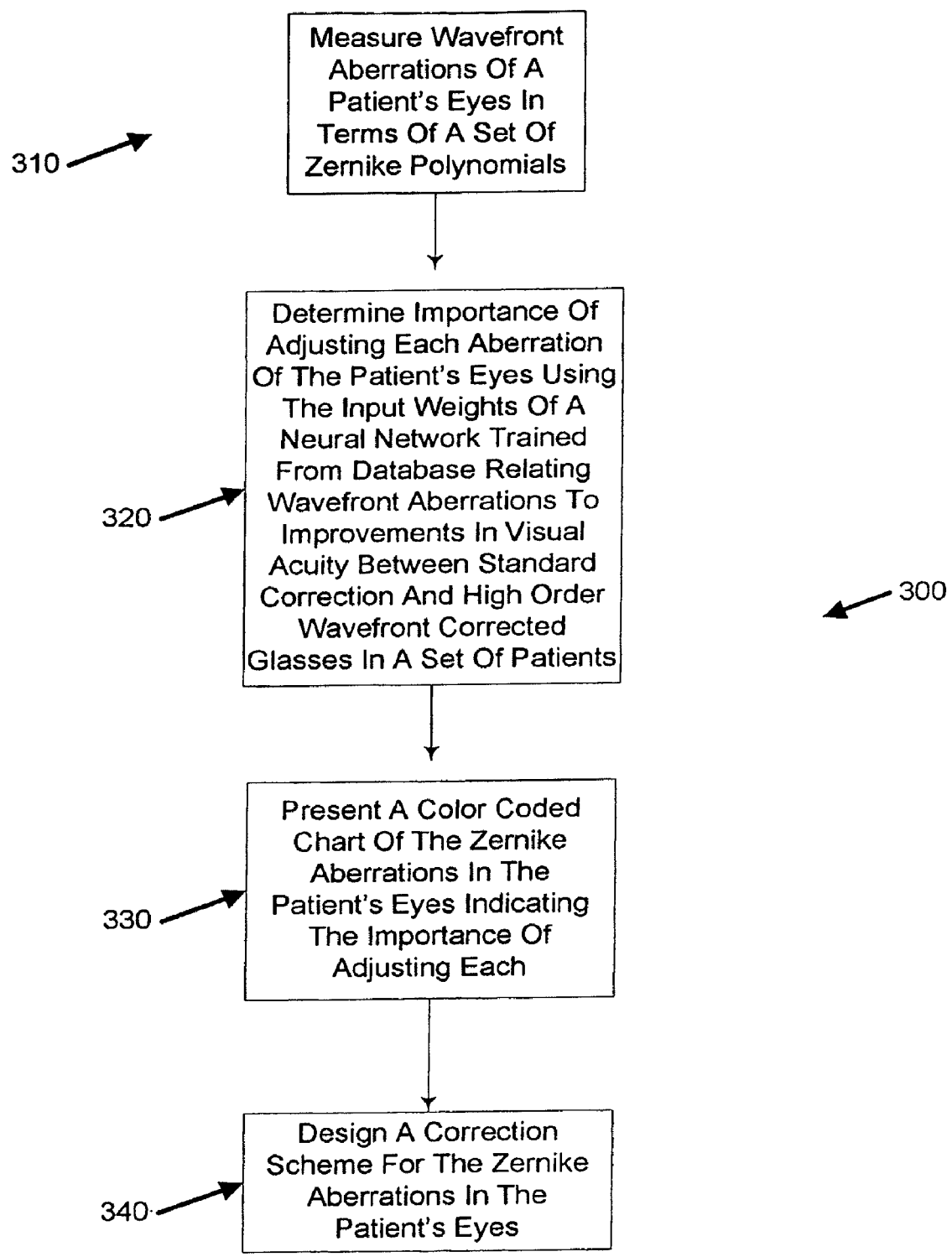
FIG. 6 is a flow chart depicting an embodiment of a process for using an embodiment of the neural network similar to that in FIG. 1 to help determine the relative importance of correcting aberrations found in a patient's eyes.

FIG. 6 is a flow chart depicting another embodiment of a process 300 for using a neural network or statistical model 100 to help determine a course of corrective action for a patient's eyes. In one embodiment, a neural network 100 is trained using some or all objectively measured Zernike aberrations as the training inputs. One or more measures of subjective visual performance, such as visual acuity, and/or contrast sensitivity are measured for each patient using traditional, low-order corrections, as with a phoropter or eyeglasses. Additionally, visual performance is subjectively measured using custom high order wavefront aberrators correcting each of the high order aberrations (e.g., spherical aberration, coma, trefoil, tetrafoil and astigmatic tetrafoil) in the input set for each patient. The difference, or the improvement measure between standard corrected vision and custom high-order aberration corrected vision, which may be low or even negative in the eye of a patient whose beneficial high order aberrations were removed, is used as the output value for each patient in the training set. Thus after training, the weights $W_{1n}$ of each of the input layer nodes 110 indicate, for each aberration, the relative importance, when the weight is positive, of correcting that aberration for improving visual acuity. In cases where the weight of the node 110 is negative, the corresponding aberration is one that improves vision, i.e. correcting the aberrations does not improve vision, but rather worsens visual acuity.

Figure 7:
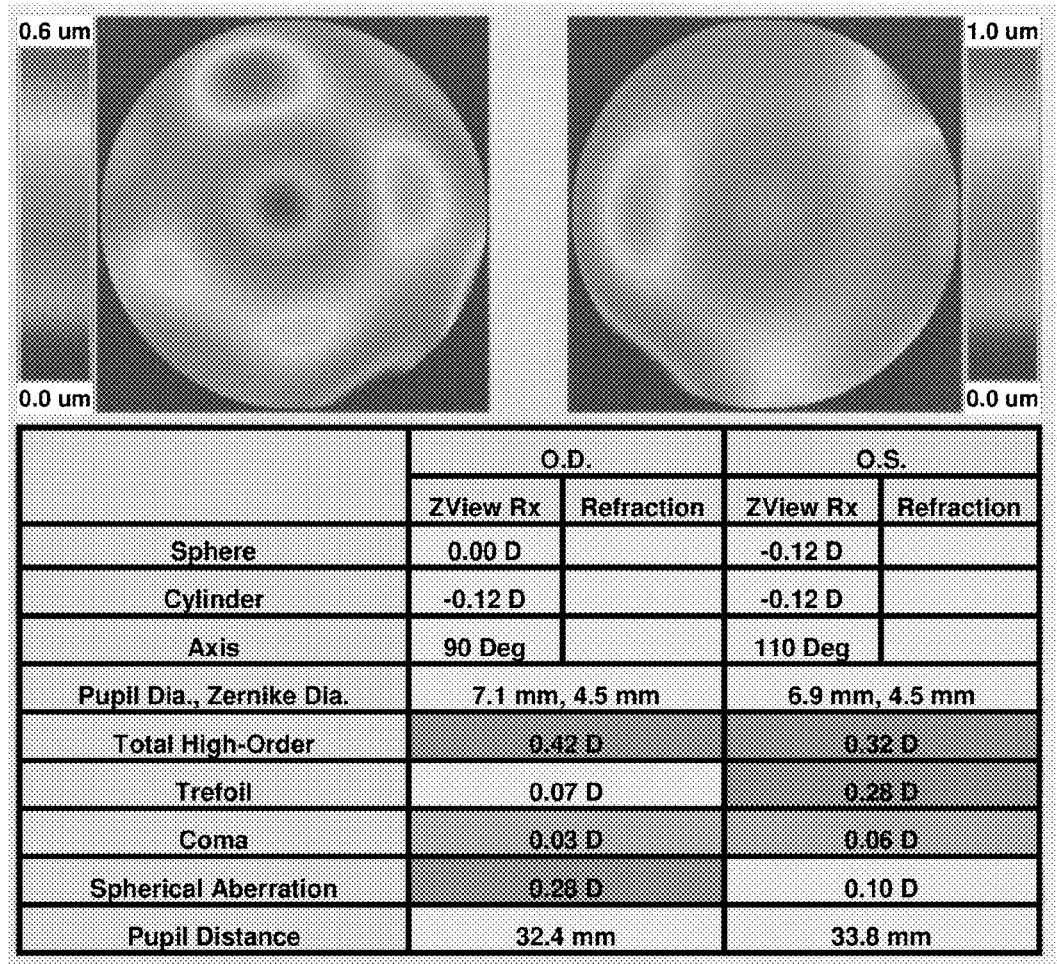
FIG. 7 illustrates a color-coded table and graphic images of high order aberrations in accordance with one embodiment of the invention.

Thus, returning to process 300, beginning at a step 310, the aberrations of a patient's eyes are measured. Moving on to a step 320, each aberration is analyzed with reference to the weights of the input layer nodes 110 of the neural network 100 trained with the aberrations as inputs and visual performance improvement as outputs and assigned an importance based on the relative magnitude and sign of the weight. Next at a step 330, a table of measured aberrations, such as Zernike polynomials in a table according to the order of the polynomial, from, for example, second order to sixth order, is presented with each aberration color coded based on the relative importance of adjusting that aberration as determined in the analysis of the step 320. FIG. 7 illustrates one example of a color-coded table and, additionally, a color-coded graphic image that illustrates high-order aberrations based on their relative importance or status (e.g., beneficial or detrimental to visual acuity), in accordance with one embodiment of the invention. Note that adjusting the aberration may include minimizing the magnitude of the aberration, increasing the magnitude of the aberration, or introducing the aberration. In one embodiment, aberrations that have small amplitudes, or that do not correlate to an improvement in vision are keyed in green, for example, aberrations having smaller, but still significant, amplitudes are keyed in yellow, for example, and aberrations having a large amplitude are keyed in red, for example, to indicate the importance of adjusting those aberrations. Note that adjusting an aberration may include decreasing the magnitude of the aberration or increasing the magnitude of a beneficial aberration. Moreover, some or all aberrations, whether present in the patient's eyes or not, may also be keyed to a color, for example, to indicate whether introducing the aberration may improve visual acuity. Moving onto a step 340, the eye care professional and the patient may use this information to develop a plan for correcting the patient's vision, and allow the eye care professional to advise the client more accurately on the value of correcting the higher order aberrations using, for example, spectacles, contacts, intraocular lenses, or surgery (e.g., LASIK). As indicated above, this correction plan may include introducing or increasing aberrations that have a beneficial impact on visual acuity.

Figure 8:
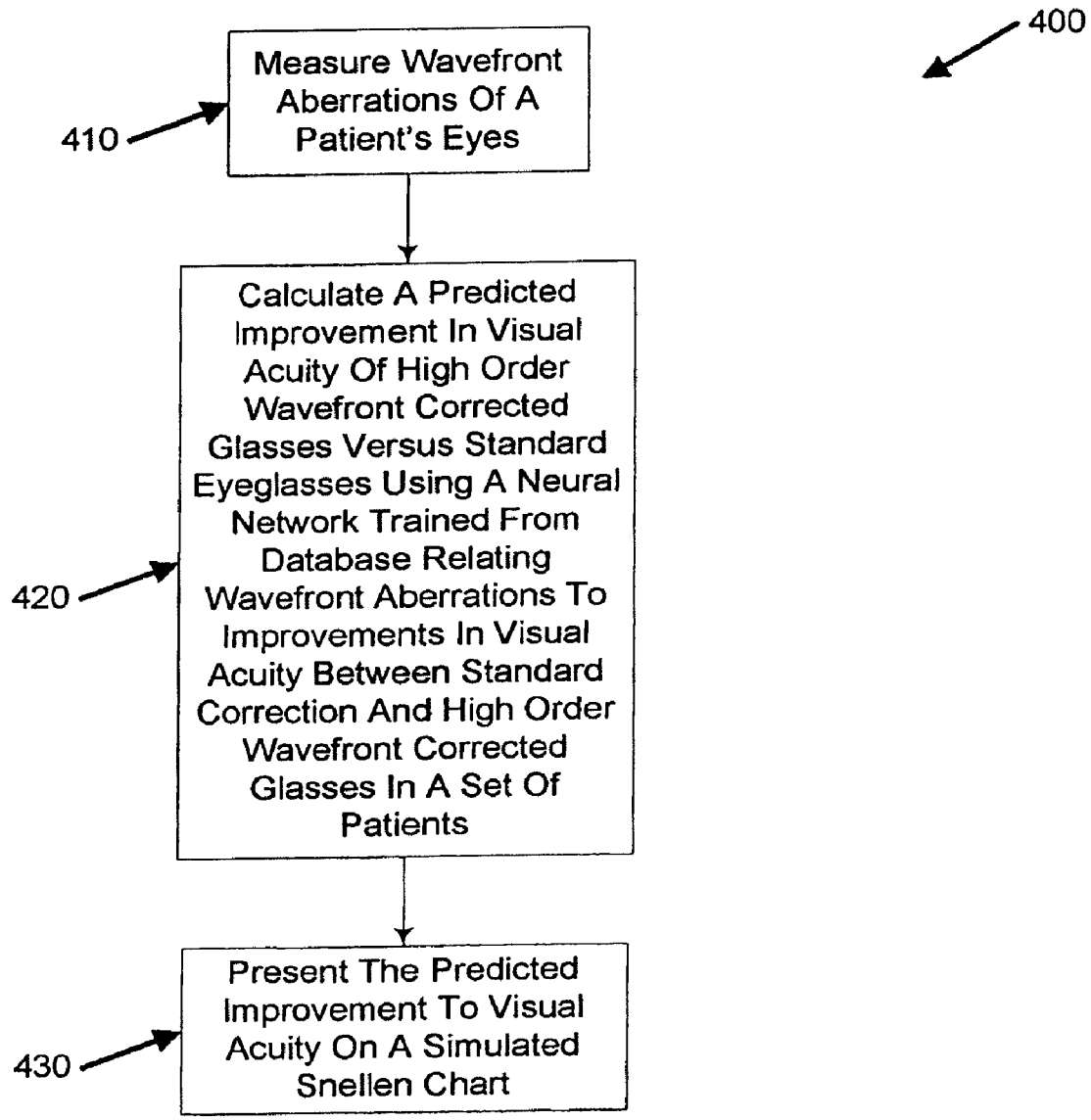
FIG. 8 depicts an embodiment of a process using an embodiment of a neural network similar to that of FIG. 1 for predicting what level of improvement in visual acuity may be obtained by a patient by choosing eyeglasses or contact lenses containing custom wavefront aberrators.
Figure 9:
FIG. 9 illustrates a graphic depiction of side-by-side comparative images of blurred vision resulting from standard correction compared to corrected vision resulting from high order aberration correction of a patient's eye, in accordance with one embodiment of the invention.

FIG. 8 depicts an embodiment of a process 400 for predicting what level of improvement in visual acuity may be obtained by a patient by choosing eyeglasses or contact lenses, for example, containing custom wavefront aberrators. An embodiment of a neural network is constructed as discussed for use in process 300 above. Starting at a step 410, the aberrations of a patient's eyes are measured. Moving to a step 420, a predicted improvement in visual acuity from using custom high order wavefront corrected glasses versus standard eyeglasses is calculated using the neural network 100. Custom high order wavefront corrected glasses include a custom wavefront aberrator that corrects the patient's vision by adjusting wavefront aberrations in the patient's visual path. This adjusting may include any combination of the following adjustments: minimizing the magnitude of existing aberrations; increasing the magnitude of existing, beneficial, aberrations; or introducing beneficial aberrations. Next at a step 430, this improvement is presented. In one embodiment, the improvement is depicted graphically in terms of the additional number of Snellen chart letters that high order corrected glasses would allow the patient to read versus standard eyeglasses. In another embodiment, a graphical depiction may be presented using a computerized display to simulate the relative blurring of the letters of the chart as shown in exemplary FIG. 9. The letters in the left chart are more blurred to indicate poorer vision resulting from standard correction or no correction. The right chart is clearer and more focused to illustrate the improved vision possible with high order aberration correction. It is understood that such graphics may provide a best approximation of a patient's visual acuity based on predicted improvement using standard correction and high-order correction, respectively. For example, if a patient's predicted improvement using standard correction is 20/25 vision and using high-order correction is 20/15 vision, for example, respective graphic charts selected (automatically or manually) to represent corresponding blurring may be presented to the patient.

In addition to being used in reference to the selection and design of custom wave front aberrator eyeglasses, embodiments of neural network 100 may also be advantageously used to predict the results of more permanent corrections, including surgical procedures and techniques such as intraocular lens insertion and corneal sculpting such as Radial Keratotomy, Astigmatic Keratotomy, Automated Lamellar Keratoplasty, Photo Refractive Keratectomy, or LASIK. The predictive ability of the trained neural network 100 is of even greater value when used in conjunction with the planning of these procedures than with custom wavefront aberrator eyeglasses due to the permanent nature of the changes that are made.

Thus, an embodiment of a process similar to the process 400 includes generating an embodiment of the neural network 100 using training data that uses improvements resulting from high-order correction in LASIK patients when compared to standard correction for those patients, measured prior to performing a LASIK procedure. Thus, a statistical model can be trained using objectively measured high order aberrations as training input values for the input layer nodes and the subjective improvement measurement values as training output values for the output node of the statistical model. After the statistical model is trained using training data, it may then be used to determine or predict the relative importance and status (e.g., beneficial, detrimental, neutral) of various high order aberrations found in LASIK patient candidates. After identifying the relative importance of the high order aberrations in the patient, the ablation pattern of the LASIK laser can be changed to optimize the patient's visual performance as a result of LASIK surgery. Further, in one embodiment of a process paralleling the process 400, the patient is presented with a visual depiction of the relative improvement (or worsening) of vision that is predicted to result from LASIK that is similar to the depictions illustrated in FIG. 9, for example. This process may be combined with steps of process 400 to provide the patient with a comparison of the predicted outcome of regular eyeglasses, LASIK (with standard or high-order correction), and of using eyeglasses incorporating custom aberrators. A process similar to process 400 may be performed for patients using or considering contact lenses or intraocular lenses. By using patients with corrective contact lenses or intraocular lenses to obtain training data, statistical models may be created to predict relative results between the different types of treatments (e.g., intraocular lenses v. regular eyeglasses v. contacts) and the different types of corrections (e.g., standard correction v. high-order aberration correction).

It is to be appreciated that in embodiments of processes of using trained neural networks, such as described herein, the computational steps comprising using the neural network 100 on a new patient, and presenting the result on a display, may be performed directly on the measurement apparatus 10 using, for example, an attached video display to present the result, or the measured aberrations may be input into another computerized system for immediate use as described herein, or for storage and later use and presentation by a different display system. Furthermore, it should be realized that, for each process disclosed herein, additional steps may be added, others removed, steps merged, or the order of the steps rearranged without departing from the scope of the invention.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

The invention claimed is:

1. A method of generating a plurality of weight values associated with respective nodes of a statistical model for use in predicting vision correction prescriptions for patients, the method comprising:
    obtaining a plurality of wavefront aberration measurements from a plurality of patient's eyes;
    obtaining a plurality of visual acuity measurements from the plurality of patients;
    applying values associated with the plurality of wavefront measurements to an input layer of the statistical model;
    applying values associated with the plurality of visual acuity measurements to an output layer of the statistical model; and
    generating the plurality of weight values associated with respective nodes of the statistical model based on the applied values associated with the plurality of wavefront measurements and corresponding values associated with the plurality of visual acuity measurements.

2. The method of claim 1 wherein the plurality of wavefront aberration measurements comprises measurements of low order aberration and one or more high order aberrations selected from a group consisting of: spherical aberration, coma, trefoil, tetrafoil and astigmatic tetrafoil.

3. The method of claim 1 wherein the statistical model is created from training data received from a plurality of patients having a common eye type.

4. The method of claim 1 wherein the statistical model comprises a neural network.

5. The method of claim 1, wherein the values associated with the plurality of visual acuity measurements comprises a plurality of difference values indicative of differences between visual acuity of patients having wavefront refraction corrected vision and visual acuity of the same respective patients having standard corrected vision, wherein wavefront refraction corrected vision comprises one or more of low and high order aberration corrected vision.

6. The method of claim 5 wherein the statistical model is capable of predicting which measured high order aberrations of the patient's eye are beneficial, detrimental or neutral.

7. A data structure created using the method of claim 1.

8. A spectacle lens constructed in accordance with the predicted vision correction prescription obtained using the method of claim 1.

9. A contact lens constructed in accordance with the predicted vision correction prescription obtained using the method of claim 1.

10. An intraocular lens constructed in accordance with the predicted vision correction prescription obtained using the method of claim 1.

11. A method of correcting a patient's vision comprising performing a surgical procedure on the patient's eye in accordance with the predicted vision correction prescription obtained using the method of claim 1.

12. A system for specifying a vision correction prescription for a patient's eye, comprising:
    means for obtaining a wavefront aberration measurement of the patient's eye;
    means for analyzing at least one value derived from the wavefront aberration measurement to predict a vision correction prescription for the patient's eye based at least in part on the at least one value, wherein the means for analyzing comprises a statistical model, wherein the statistical model comprises:
    a plurality of wavefront aberration measurements from a plurality of patient's eyes;

a plurality of visual acuity measurements from the plurality of patients;

values associated with the plurality of wavefront measurements, wherein the values associated with the plurality of wavefront measurements are applied to an input layer of the statistical model;

values associated with the plurality of visual acuity measurements, wherein the values associated with the plurality of visual acuity measurements are applied to an output layer of the statistical model; and a plurality of weight values associated with respective nodes of the statistical model, wherein the plurality of weight values are generated based on the applied values associated with the plurality of wavefront measurements and corresponding values associated with the plurality of visual acuity measurements.

13. The system of claim 12 wherein the statistical model comprises a neural network.

14. The system of claim 12 wherein the measured wavefront aberration may be expressed with Zernike polynomials of the second order representing low order aberration and third order or higher representing high order aberrations.

15. The system of claim 12 wherein the predicted visual correction prescription comprises spherical, cylindrical and axis parameters associated with a standard prescription.

16. The system of claim 15 wherein the predicted vision correction prescription further prescribes adjusting at least one high order aberration associated with the patient's eye.

17. The system of claim 16 wherein adjusting comprises one selected from the group consisting of minimizing, increasing, and introducing the at least one high order aberration.

18. The system of claim 12 further comprising means for providing a graphic illustration of at least one high order aberration, wherein the graphic illustration comprises a color-coded table depicting a relative importance of the at least one high order aberration.

19. The system of claim 12 wherein the statistical model is capable of predicting whether a measured high order aberration of the patient's eye is beneficial, detrimental or neutral.

* * * * *